United States Patent
Chuter (12) 
(10) Patent No.: US 6,517,574 B1
(45) Date of Patent: Feb. 11, 2003

(54) SYSTEM AND METHOD FOR ENDOVASCULAR ANEURYSM REPAIR IN CONJUNCTION WITH VASCULAR STABILIZATION

(75) Inventor: Timothy A. M. Chuter, Burlingame, CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 0 days.

(21) Appl. No.: 10/108,184

(22) Filed: Mar. 25, 2002

Related U.S. Application Data (63) Continuation of application No. 09/559,032, filed on Apr. 27, 2000, now Pat. No. 6,361,556.

(51) Int. Cl.[7] .................................. A61F 2/06
(52) U.S. Cl. ..................... 623/1.23; 623/1.11
(58) Field of Search ............... 623/6.11–6.22, 623/1.23; 606/200, 194, 191, 198, 192

(56) References Cited

U.S. PATENT DOCUMENTS

| | | | |
|---|---|---|---|
| 5,211,658 A | 5/1993 | Clouse | |
| 5,489,295 A | 2/1996 | Piplani et al. | |
| 5,527,355 A | 6/1996 | Ahn | |
| 5,562,724 A | 10/1996 | Vorwerk et al. | |
| 5,562,728 A | 10/1996 | Lazarus et al. | |
| 5,693,088 A | 12/1997 | Lazarus | |
| 5,843,170 A | 12/1998 | Ahn | |
| 5,944,750 A | 8/1999 | Tanner et al. | |
| 5,968,090 A | 10/1999 | Ratcliff et al. | |
| 5,993,481 A | * 11/1999 | Marcade et al. | 623/1.11 |
| 6,197,046 B1 | * 3/2001 | Piplani et al. | 623/1.11 |
| 6,214,036 B1 | * 4/2001 | Letendre et al. | 623/1.11 |

\* cited by examiner

*Primary Examiner*—Olik Chaudhuri
*Assistant Examiner*—Hoa B. Trinh
(74) *Attorney, Agent, or Firm*—Fulwider Patton Lee & Utecht, LLP (57) ABSTRACT

The present invention is a device and method for installing a graft within a vascular lumen of a patient so as to substantially reduce fluid flow around the graft and axial migration of the graft.

By first deploying a substantially rigid stent within the vascular lumen of the patient so as to expand the vascular lumen beyond its initial natural diameter, the substantially rigid stent is thereby frictionally engaged to the wall of the vascular lumen. A graft is then deployed within the lumen of the substantially rigid stent, with the graft's attachment system being at substantially the same longitudinal level within the target vessel as the substantially rigid stent.

21 Claims, 10 Drawing Sheets

SYSTEM AND METHOD FOR ENDOVASCULAR ANEURYSM REPAIR IN CONJUNCTION WITH VASCULAR STABILIZATION

This application is a continuation, and claims the benefit of U.S. Application Ser. No. 09/559,032, filed Apr. 27, 2000, now U.S. Pat. No. 6,361,556, the contents of which are incorporated herein by this reference.

BACKGROUND OF THE INVENTION

The present invention relates to systems which are used for repairing defects in vessels and other lumens. More particularly, the present invention relates to methods and systems for the endovascular repair of a vascular defect, while simultaneously stabilizing the vascular site at which an intraluminal graft is attached.

Aneurysms are discrete dilations of the vascular wall. One of the most common, and among the most life threatening, is an aneurysm of the abdominal aorta between the renal and iliac arteries. If untreated, the aneurysm dilates progressively with an ever increasing risk of rapture and hemorrhagic death.

One method of treatment is provided by direct surgical intervention, in which the defective vessel may be bypassed or entirely replaced using a prosthetic device such as a synthetic graft. The risks involved in direct surgical intervention of this magnitude are great, and include an extensive recovery period.

In recent years a less invasive method of treatment has evolved through a series of inventions. The details vary, but, conventionally, a resilient tubular conduit fashioned from flexible fabric (herein referred to as a "graft") is introduced into the defective vessel by means of catheters introduced into the femoral artery. The graft is attached to the non-dilated arteries above and below the aneurysm using expandable metallic cylinders (herein referred to as "attachment systems") which may include barbs or hooks to assist attachment to the vascular wall. Conventionally, an attachment system is attached to the interior of the graft's lumen.

However, the use of tubular grafts to reinforce vascular walls in a patient is attended by numerous complications. The most troubling long-term complications include difficulty in forming an adequate connection of the graft to the vascular wall, which may result in fluid leakage around the exterior of the implanted graft, and downstream migration of the graft. There are certain factors which contribute to these complications. In particular, there may be a slow but steady increase in the diameter of the vessel at the site of a stent-graft attachment, particularly when the attachment system is self-expanding, and it is not yet clear whether the diameter reaches a stable limit. As a result of this steady increase in the vascular diameter, an attachment to the vessel which might initially be adequately secure will tend to loosen, increasing the probability of graft migration and fluid leakage around the graft.

Accordingly, there exists a need to stabilize a vessel being repaired against gradual dilation, and to enhance the connection between a repair device and the vascular wall. The present invention addresses these needs.

SUMMARY OF THE INVENTION

Briefly, and in general terms, the present invention provides a system and method for endovascular repair involving vascular stabilization of a repair site. It is contemplated that aortic stabilization may be achieved by first implanting at a desired location within the vessel of a patient a substantially rigid stent, or a vascular support structure configured such that it does not have a tendency to continue to expand after implantation. A graft is thereafter contemplated to be implanted within the vessel at the repair site.

It has been discovered that when a stent that does not have a tendency to continue to expand after implantation is deployed within a vessel of a patient there is an immediate increase in the diameter of the vessel accompanying expansion of such stent, but there is little change in the diameter of the vessel thereafter. Moreover, it has been discovered that such stabilizing structure is rapidly incorporated into the vascular wall by a process referred to as tissue ingrowth. The present invention harnesses this physiological behavior of the vessel.

In one aspect of the present invention, stabilizing structures embodying a substantially rigid stent, which has sufficient stiffness to retain a fixed expanded diameter, is deployed by endovascular insertion at a location within a vessel. The substantially rigid stent of the present invention is configured to have numerous orifices in its wall in its expanded state. These orifices facilitate incorporation of the stent into the vascular wall, and allow attachment systems of a subsequently implant graft to protrude through the wall of the stent. Next, a flexible tubular graft with an expandable attachment system is provided. The graft and the attachment system assembly is deployed by endovascular insertion within the vessel so as to allow the attachment system to engage the vessel. The attachment system may have hooks, or any protrusion, structure or surface treatment, that provides fixation of the graft and attachment system relative to the substantially rigid stent.

Once the substantially rigid stent is implanted in the corporeal vessel, the vessel maintains a constant diameter established by the diameter of the substantially rigid stent. Moreover, over a period of time, the vessel may incorporate the substantially rigid stent into its wall, thereby enhancing the resistance of the substantially rigid stent to downstream forces. Thus, the attachment system fixing the graft in place within the vascular lumen has the advantage of being provided with a stable foundation which eliminates the slow radial dilation of the vessel which might occur in the absence of such stent. Additionally, the structure of the substantially rigid stent may also reinforce the vascular wall in the downstream direction and provide the attachment system of a graft with additional mechanical support to resist downstream forces.

These and other objects and advantages of the invention will become apparent from the following more detailed description, when taken in conjunction with the accompanying drawings of illustrative embodiments.

DETAILED DESCRIPTION OF THE PREFERRED EMBODIMENTS

The present invention is directed to a system and method for endovascular repair involving stabilizing a patient's vessel at a site at which a graft is attached to the vessel. It will be appreciated that, while the description which follows relates to the aorta of a patient, the invention may equally be applied to any defective vessel or body lumen of a patient. The preferred embodiments of the system and method of the present invention are described below.

Figure 1:
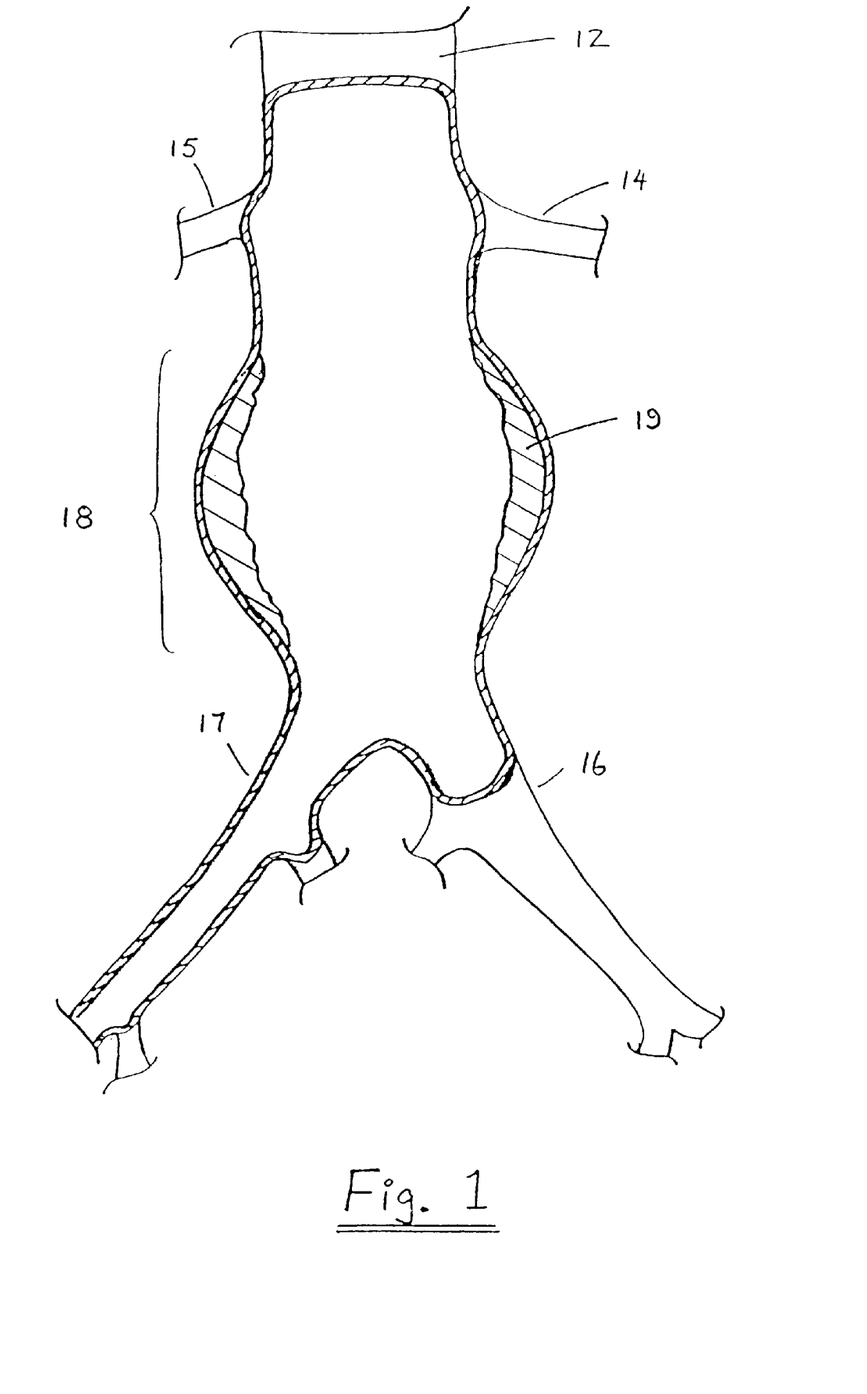
FIG. 1 is a cross-sectional view of the vascular system of a patient, depicting the relationship of an aorta to renal and the iliac arteries.

One possible site for the use of the present invention is exemplified in FIG. 1, which is a schematic depiction of the vascular system of a patient showing the relationship of the aorta 12 to the renal arteries 14, 15 and the iliac arteries 16, 17 and also showing a portion 18 of the aorta 12 dilated by an aneurysm. A lining of thrombus 19 is shown adhering to the dilated portion of the aorta 12.

It has been noted herein that implanting a graft into an aorta (or other lumen) may be attended by complications which are caused by a tendency of the vascular lumen to gradually dilate. Such dilation of the vascular lumen may cause the graft to migrate downstream, and, further, may cause fluid to leak around the outside of the graft. However, it has been discovered that, when stents or other vascular support structures that do not have a tendency to continue to expand after implantation are employed, the result is different. With such structures, there is an immediate increase in the diameter of the vessel upon implantation of the structure, but there is little change in the diameter of the vessel thereafter. Stabilizing structures having the characteristic of remaining with a substantially fixed diameter after deployment shall be referred to herein generally as "substantially rigid stents." Substantially rigid stents are conventionally deployed by balloon-expansion delivery systems, but may also be deployed by other mechanical systems.

Moreover, it has been discovered that substantially rigid stents which have a wall which includes a plurality of orifices and which are not separated from the vascular wall by the fabric of a graft or other structure, are rapidly incorporated into the vascular wall by a natural process in which the tissue of the vessel grows through such orifices and surrounds the filaments of which the stent is composed. The present invention, therefore, is configured to harness this physiological behavior of the vessel in order to provide a stable site for subsequent implantation of a graft or other prosthesis.

Figure 2:
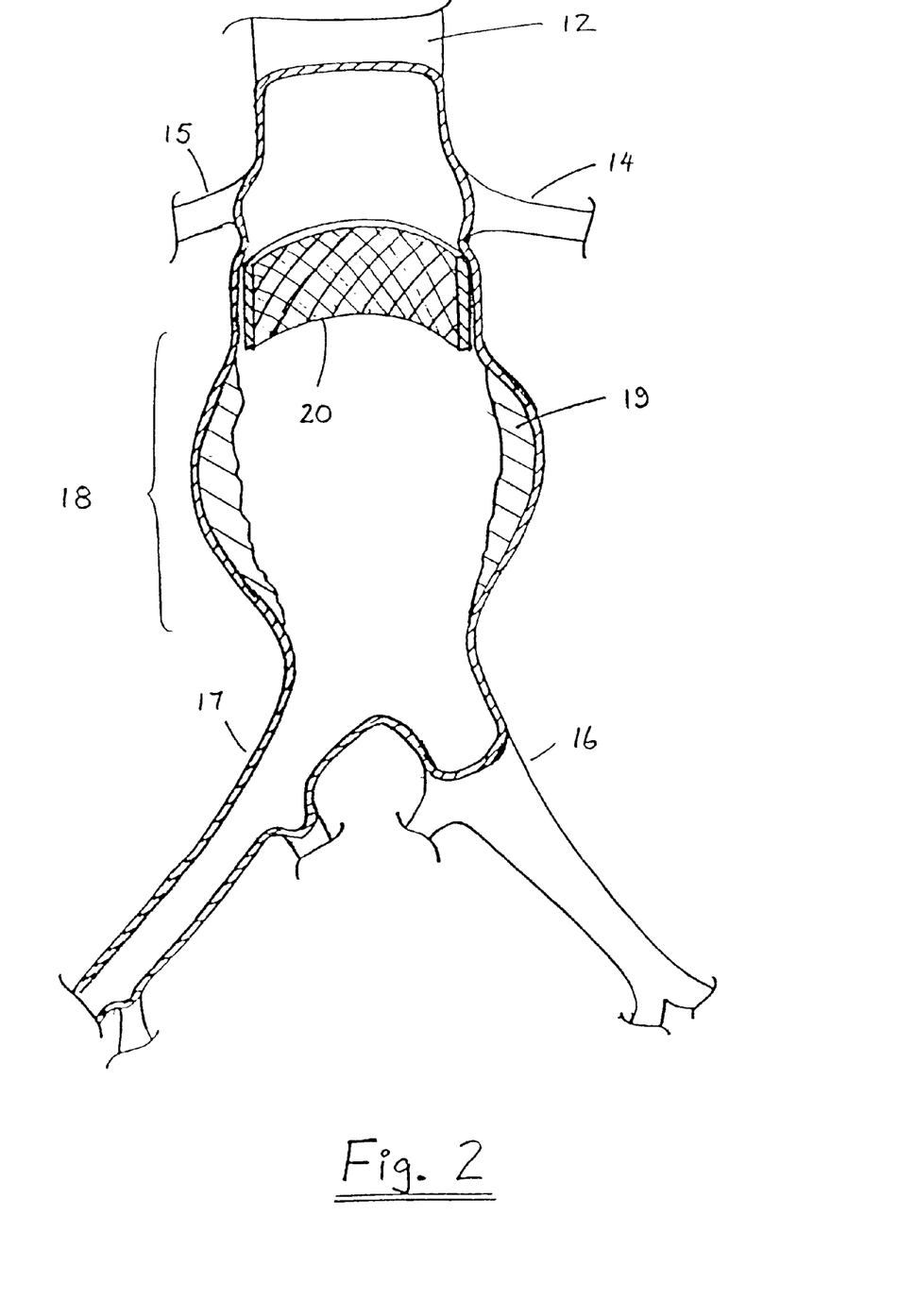
FIG. 2 is a cross-sectional view, depicting a stabilizing stent implanted in the aorta according to the present invention.

Thus, in accordance with the present invention, a substantially rigid stent 20 having a generally tubular configuration is deployed at a desired location within a healthy section of an aorta 12, as exemplified in FIG. 2. Substantially rigid stents 20, and methods for deploying them, are known in the art. The substantially rigid stent 20 of the present invention, in accordance with conventional methods of manufacture, is formed of a biocompatible material which will deform by radially expanding under pressure applied by a balloon or other mechanical system, but which will, after deployment, maintain a fixed diameter and resist deformation from forces imposed by the vascular environment. It is contemplated that the substantially rigid stent 20 of the present invention includes a plurality of orifices in its wall when in an expanded condition. Upon deployment, the stent 20 is expanded to dilate the diameter of the vessel 12. Such dilation has been found to have the desired effect of anchoring the stent 20 without injury to the vessel 12.

After the substantially rigid stent 20 is deployed within the vessel 12, an endovascular graft 22 configured with an expandable attachment system 24 may be implanted at the repair site, although any prosthetic device can be subsequently implanted. Many endovascular grafts are well known in the art, and may be manufactured from any surgical implantable material (such as Dacron™) which is known to be sufficiently biologically inert, non-biodegradable, and durable.

Figure 3:
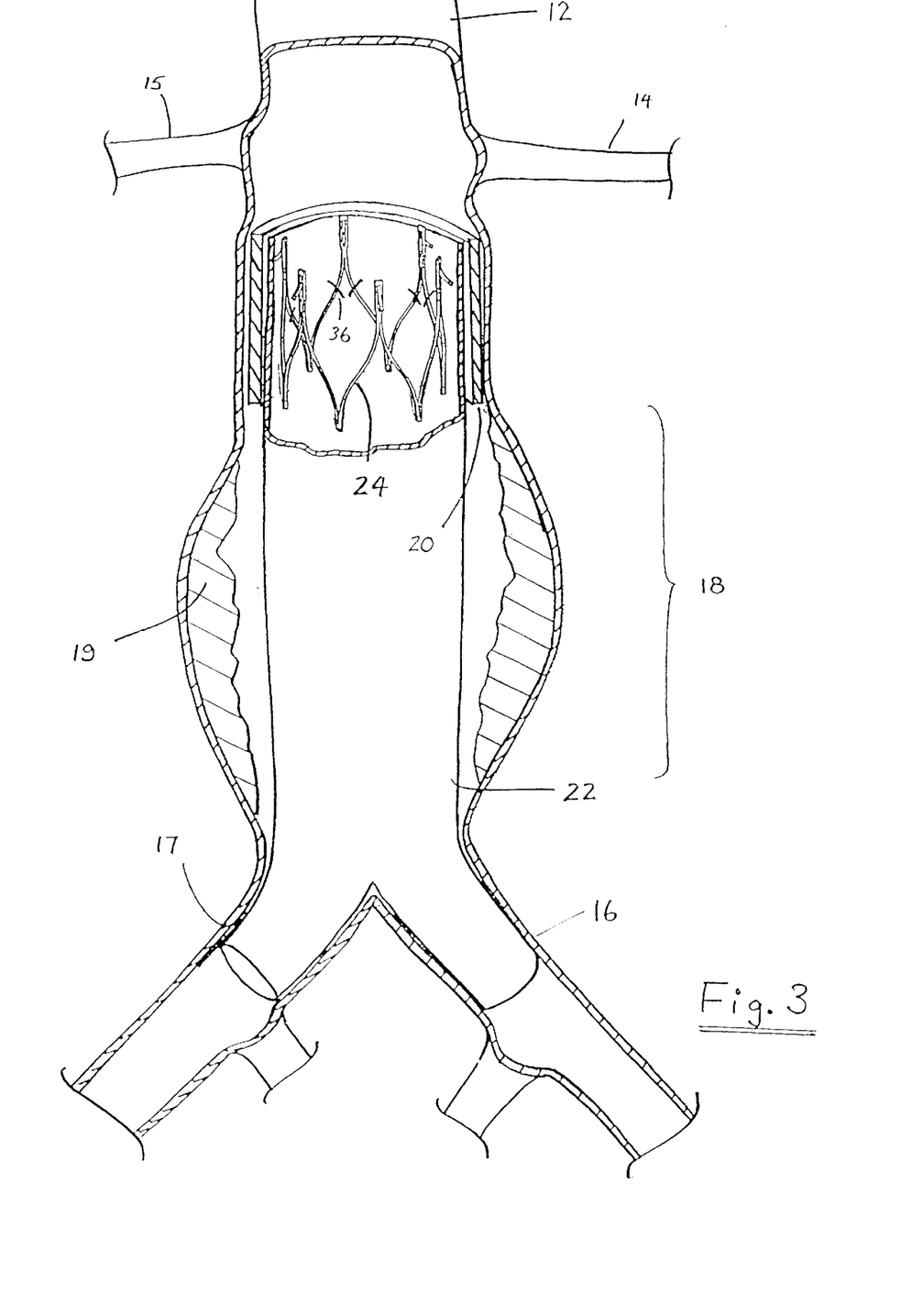
FIG. 3 is a partial cross-sectional view depicting an endovascular graft with an attachment system implanted within the aorta in contact with the stabilizing stent.

In one aspect, the endovascular graft 22 may be bifurcated with right and left branches 26, 27 adapted to protrude into each of the iliac arteries 16, 17 as exemplified in FIG. 3, or, in another aspect, may embody a simple tubular shape, or, in yet a further aspect may be a tapered aorto-iliac tubular graft as known in the art. The attachment system 24 of the present invention is self-expanding in the preferred embodiment, but may be balloon-expanded. Self-expanding attachment systems are known in the art, and are conventionally formed of a corrosion resistant material which has good spring and fatigue characteristics such as Elgiloy™, steel or Nitinol.

Figure 8:
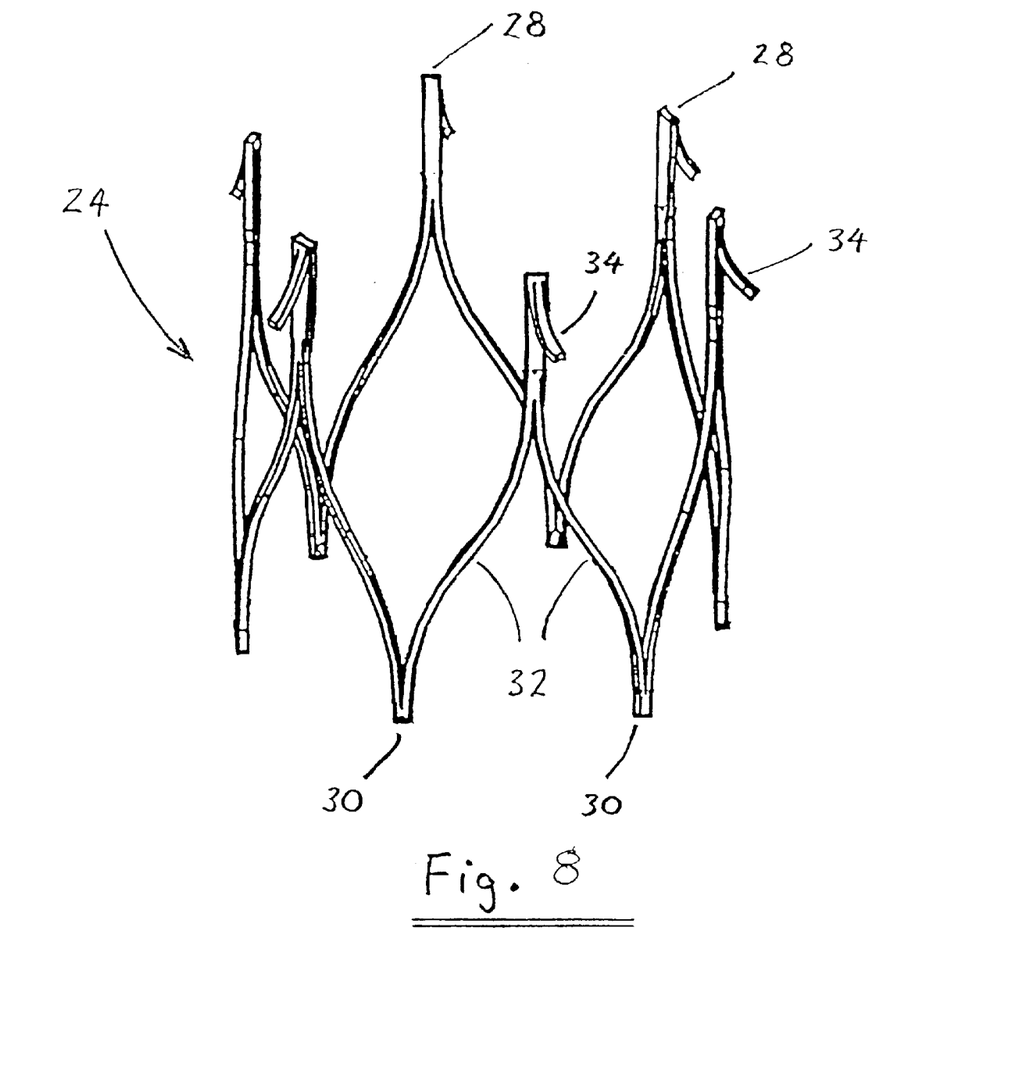
FIG. 8 is a perspective view of one embodiment of an attachment system for use with the present invention.
Figure 9:
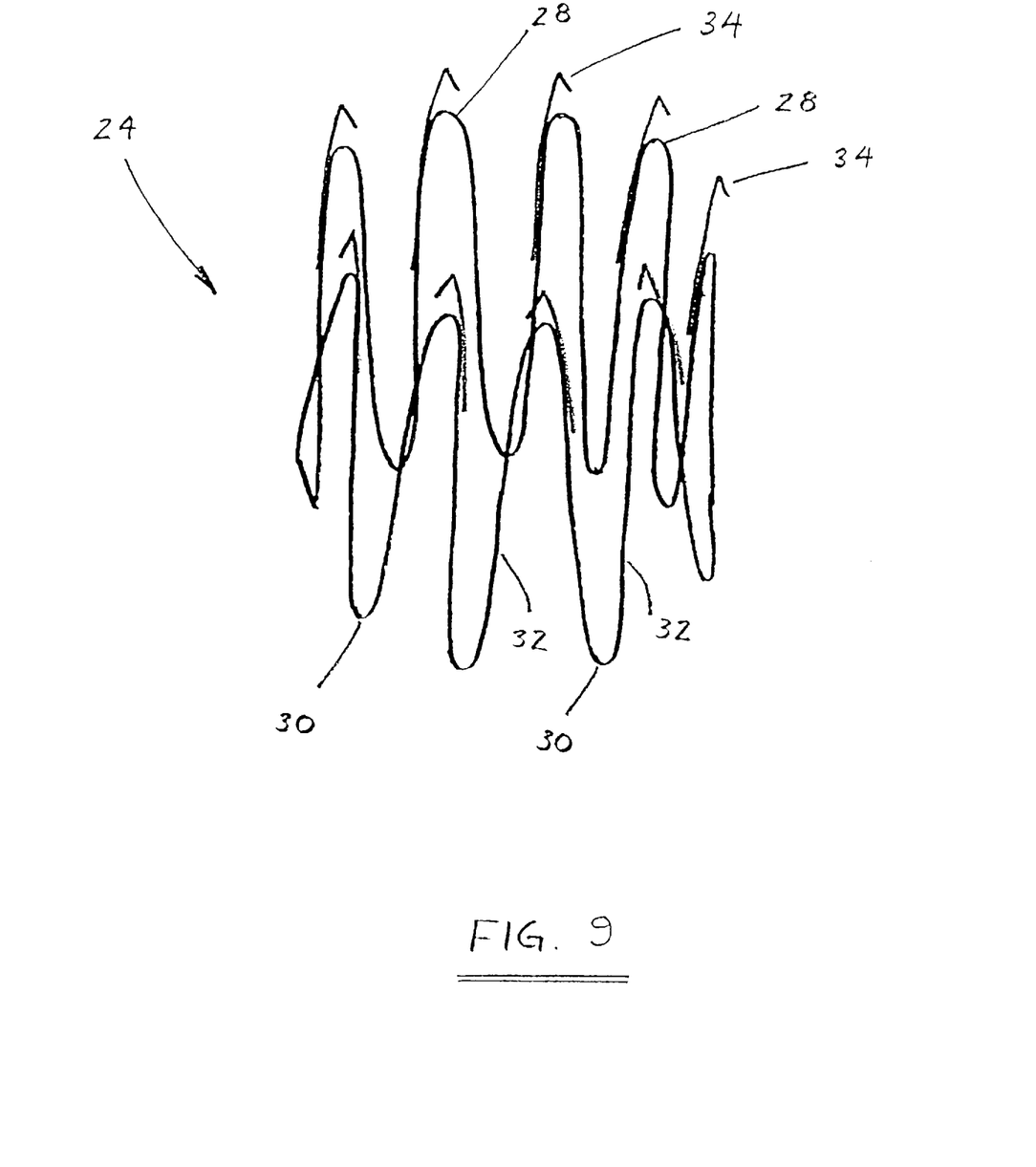
FIG. 9 is a perspective view depicting another attachment system for use with the present invention.

As shown in more detail in FIGS. 8 and 9, the self-expanding attachment system 24 may be formed from a frame which follows a generally undulating path within a cylindrical profile and embodying a plurality of alternating superior apices 28 and inferior apices 30 which are joined by connecting legs 32. When the attachment system 24 is compressed radially inward, its legs 52 and apices 30 are urged radially outward in a direction at right angles to its longitudinal axis. Additionally, hooks 34 may be connected to the attachment system 24 to enhance its ability to attach to a vessel wall.

As shown in FIG. 3, the attachment system 24 may be configured within the lumen of the graft 22 at a superior end portion thereof, and may be connected thereto by connectors 36 formed of stitches of Dacron™ polyester suture or other suitable material. The graft 22 and its attachment system 24 assembly is deployed within the aorta 12 so as to allow the attachment system 24 to urge the graft 22 to an expanded position and to engage the substantially rigid stent 20 at or near substantially the same longitudinal position as the substantially rigid stent 20 to form a seal between the graft/stent/aorta. Where hooks 34 are provided, the same operates to engage the stent and engage the aorta. The substantially rigid stent 20 may be encased in aortic tissue. The hooks will engage both stent and aorta eventually after tissue ingrowth. Such hooks 34 may be configured to protrude through the wall of the graft 22 or may extend beyond a leading edge of the graft 22.

Figure 10:
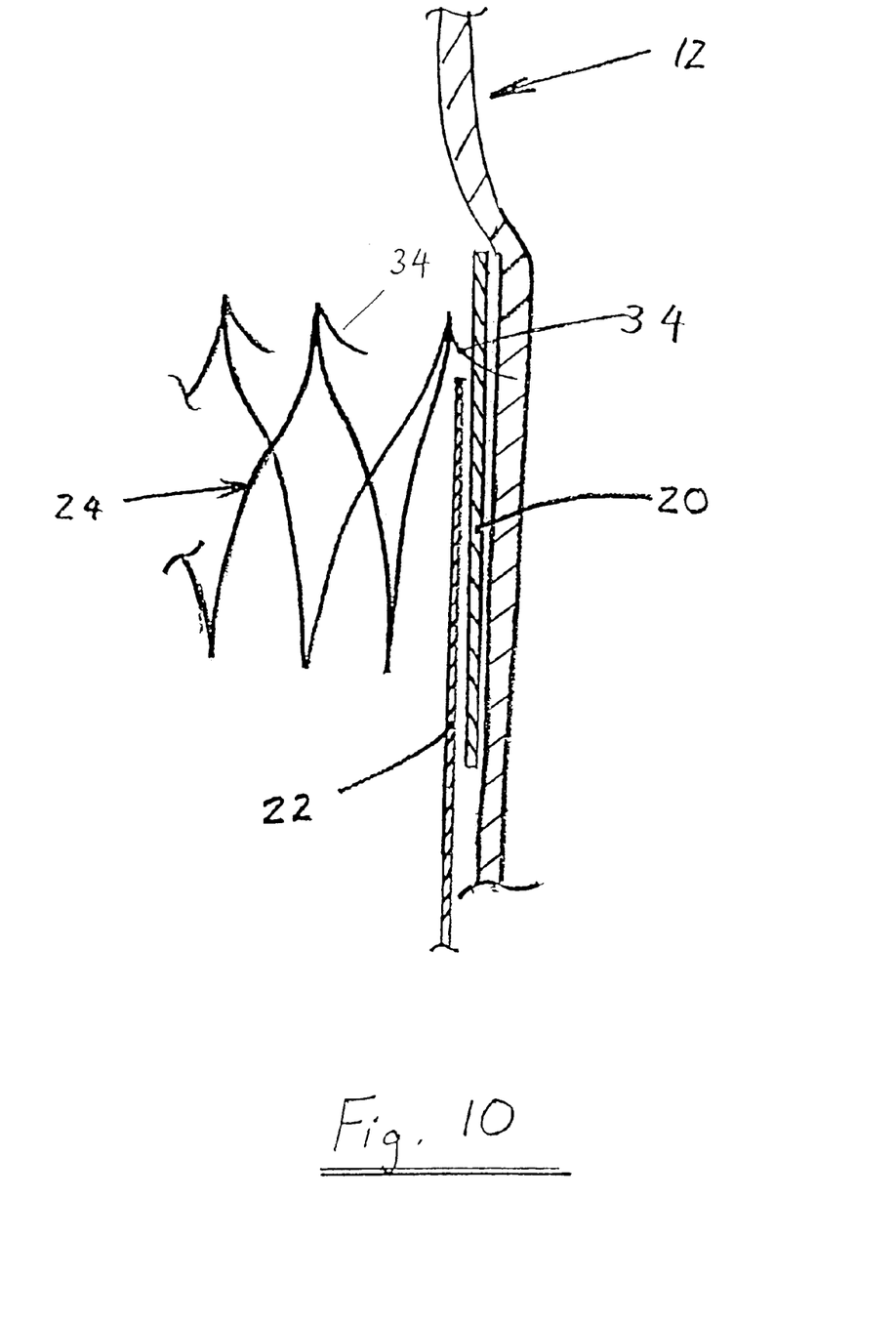
FIG. 10 is a partial cross-sectional view, depicting the juxtaposition of a substantially rigid stent, and a graft, with attachment system of the present invention.

As previously noted, the substantially rigid stent 20 of the present invention is configured to have numerous orifices when in its expanded condition. Thus, it is contemplated that each hook 34 of the attachment system 24 may protrude separately through an orifice of the stent 20 to thereby penetrate the aortic wall 12 (FIG. 10). Additionally, the attachment system 24 of the present invention is manufactured so that it is substantially unable to impart a radially outward force sufficient to cause the substantially rigid stent 20 to continue to expand beyond the expansion profile assumed upon its deployment. Where the attachment system 24 is self-expanding, any continued self-expansion is precluded by the substantially rigid stent 20. Such forces generated by the attachment system 24, however, can facilitate the creation of desired sealing.

Figure 4:
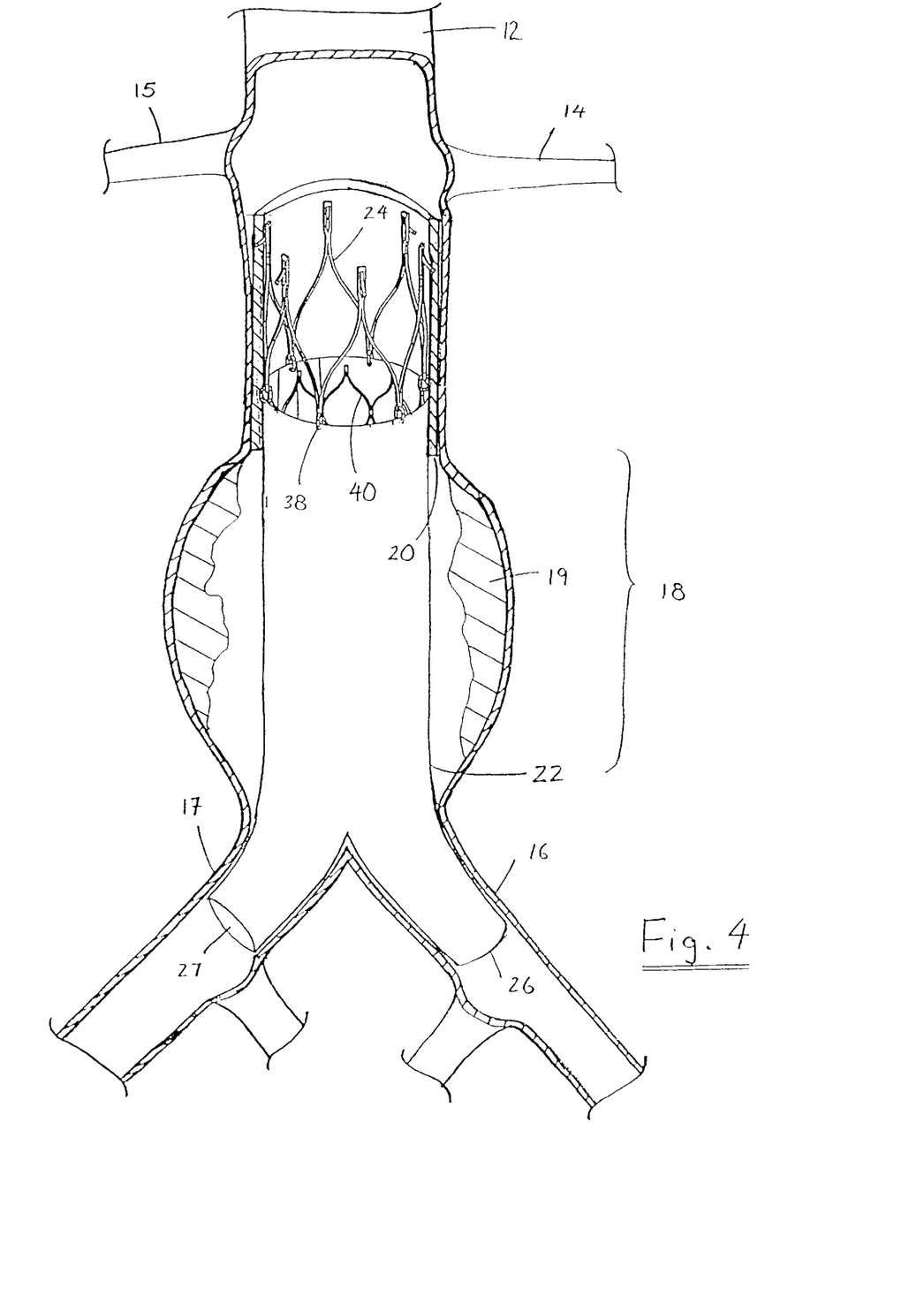
FIG. 4 is a partial cross-sectional view, depicting an alternative embodiment of a graft assembly positioned within the aorta.
Figure 5:
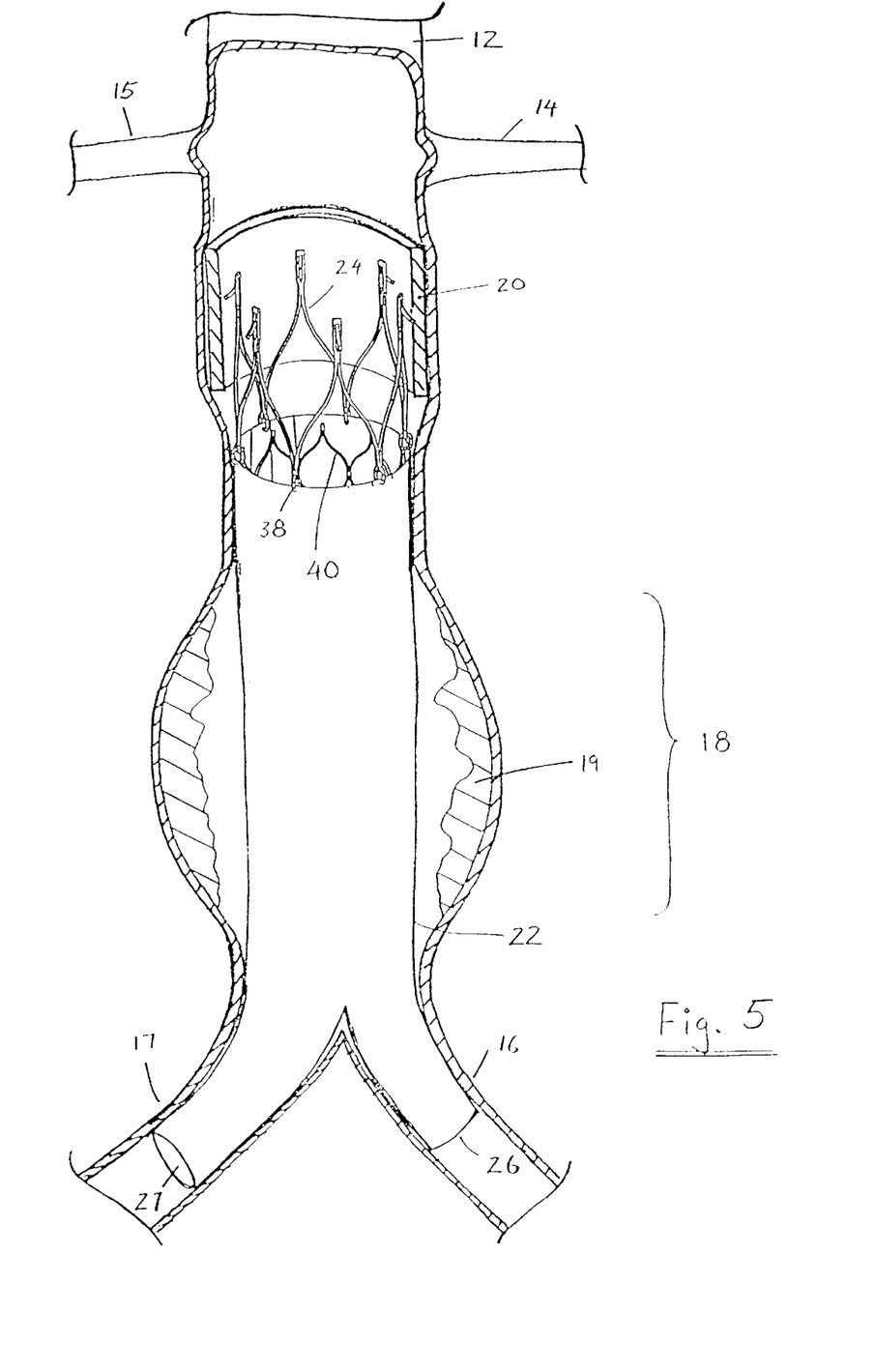
FIG. 5 is a partial cross-sectional view, depicting the embodiment of a graft assembly of FIG. 4, positioned so that the graft does not overlap with the substantially rigid stent.

In a further aspect of the present invention (FIG. 4), the attachment system 24 may be connected to the graft 22 so as not to overlap with the graft, but be positioned with its distal end in close proximity with or in abutting relationship with the superior end of the graft. Connection between the attachment system 24 and the graft 22 may be achieved by means of ties 38, which may be formed of loops of Dacron™ polyester suture or other suitable material. The advantage of not having an overlap between graft 22 and attachment system 24 is that the profile of the graft 22 in compressed condition is reduced, thus presenting a more favorable profile for insertion and deployment within the vascular system. In one variation of this aspect of the invention (FIG. 4), the graft 22 may be positioned to overlap with the substantially rigid stent 20. In another variation (FIG. 5), the graft may be positioned inferior of the stent, so as not to overlap with it. In these aspects, where there is no overlap between graft 22 and attachment system 24, support structures 40 may be added in order to seal the graft to the vascular wall and maintain the patency of the graft's lumen. The support structures 40 may be similar in overall configuration to the attachment systems exemplified in FIGS. 8 and 9, but will not include the hooks that the attachment systems may have. Wherever they are required within the graft 22 (including within the left and right branches 26, 27), a plurality of support structures 40 may be used, and may be delivered simultaneously with the graft positioned within the lumen of the graft, or may be delivered and positioned within the lumen of the graft after the graft has been deployed. Methods of delivering support structures to the lumen of a graft after a graft has been delivered are well known in the art, and will not be described here.

Figure 6:
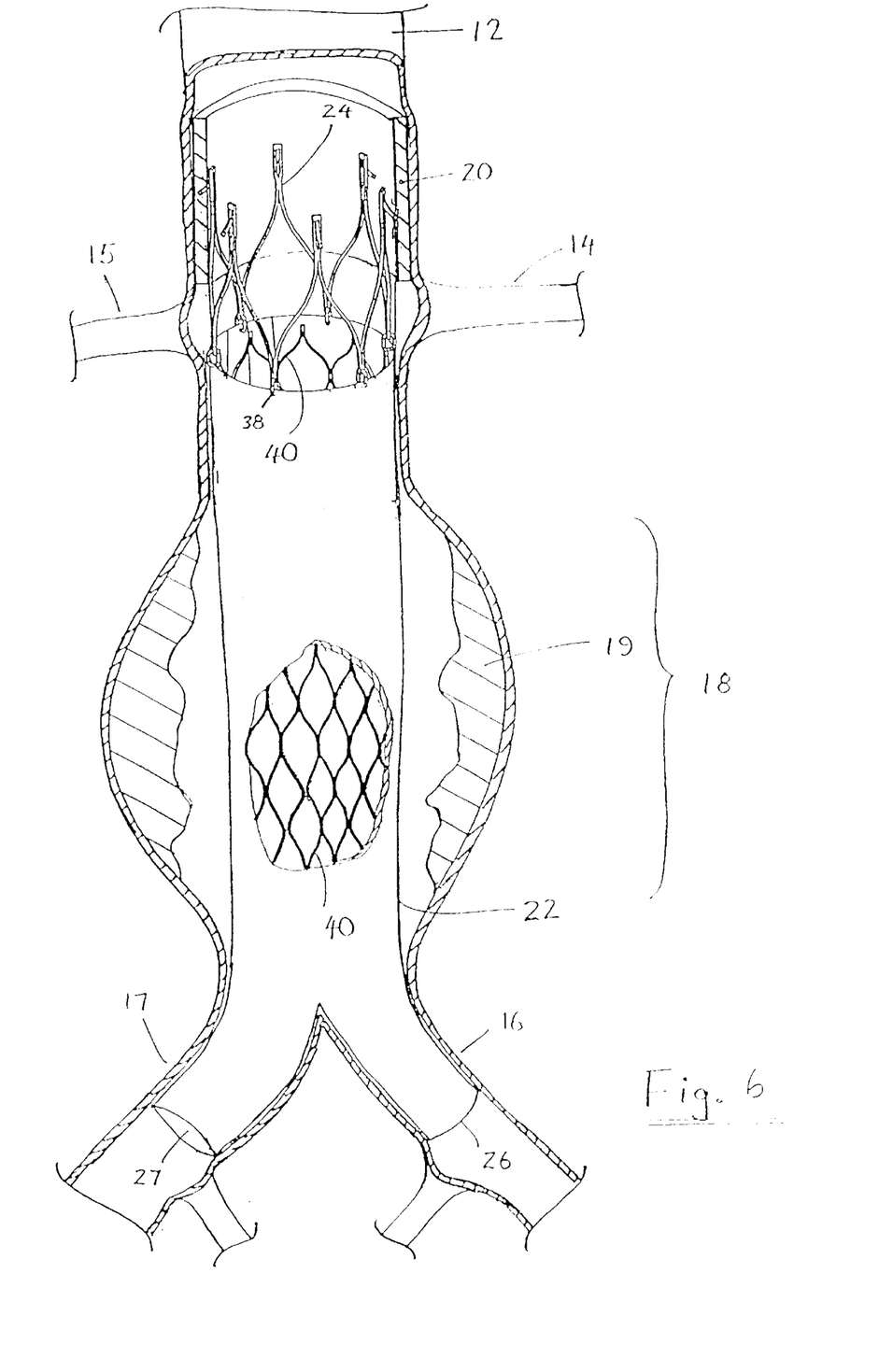
FIG. 6 is a partial cross-sectional view, depicting the embodiment of a graft assembly of FIG. 4, positioned so that the attachment system attaches to the aorta above the renal arteries.
Figure 7:
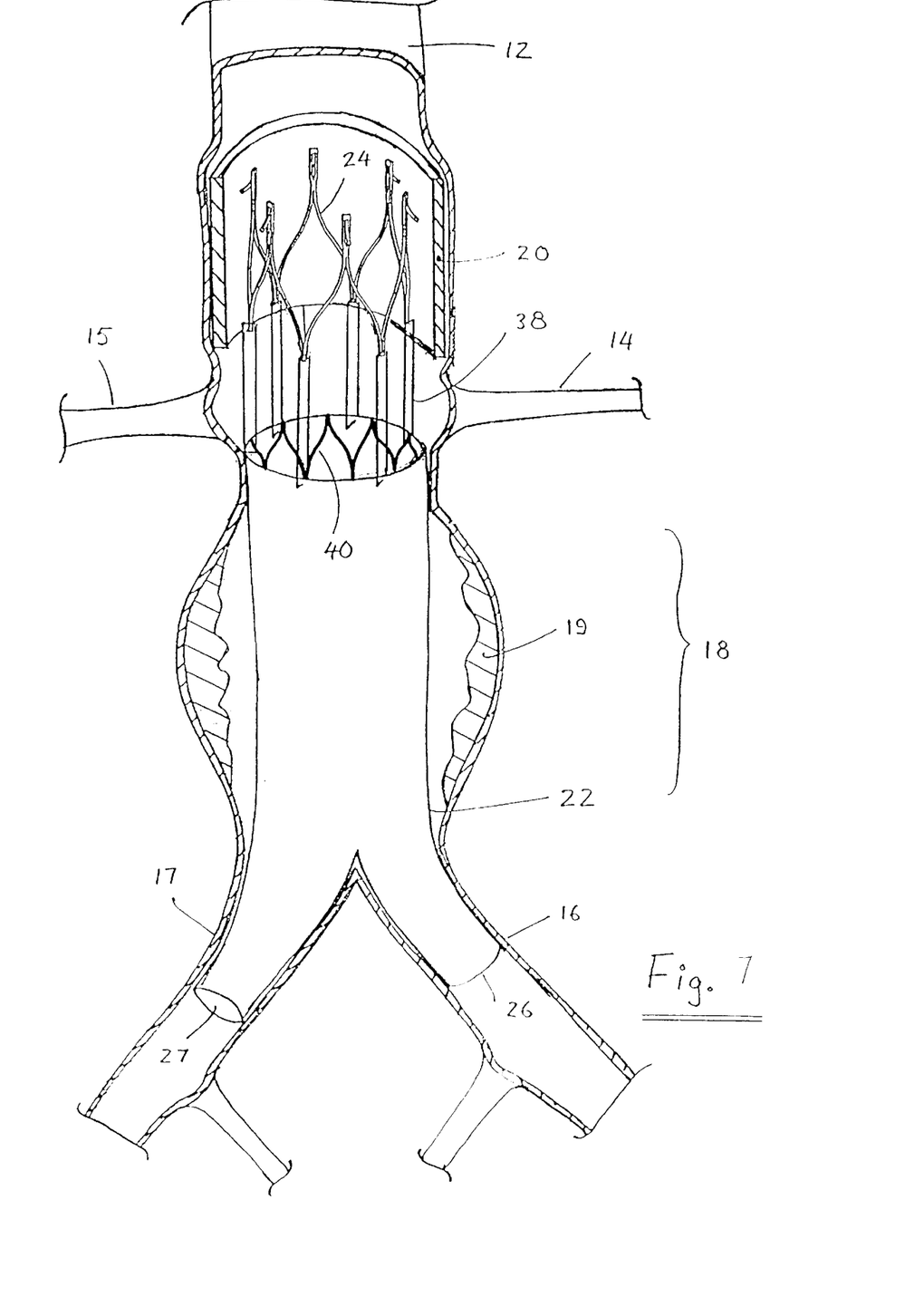
FIG. 7 is a partial cross-sectional view, depicting yet a farther embodiment of a graft assembly positioned within the aorta.

Additionally, as shown in FIG. 6, the attachment system may be positioned superior of the renal arteries 14, 15, for example, while the graft 22 is positioned entirely inferior of the renal arteries 14, 15. It will be appreciated that, in this situation, the substantially rigid stent 20 would also be positioned proximal of the renal arteries. This aspect of the invention may be used in cases where the aortic wall below the renal arteries 14, 15 does not present sufficient healthy material to form an adequate attachment. The portions of metal elements comprising the attachment system 24 which might extend across the orifices of the renal arteries 14, 15 are narrow in profile, and would not form a substantial barrier to fluid flow into the renal arteries 14, 15. Alternatively, the ties 38 could be lengthened as shown in FIG. 7, in order to longitudinally separate the attachment system 24 from the graft 22. Where the length of the ties 38 is extended as exemplified in FIG. 7, the graft 22 can advantageously assume a position that is axially at an angle with respect to the attachment system 24, where necessary.

Once the graft 22 is fixed to the aortic wall 12 by the attachment system 24 at the longitudinal level of the substantially rigid stent 20, the attachment system 24 benefits from the resistance to aortic dilation provided by the substantially rigid stent 20, and also benefits from the resistance to downstream forces provided by the substantially rigid stent 20. Thus, the system and method disclosed by the present invention has the advantage of reducing the likelihood of downstream migration of the graft and of leakage around the outside of the graft.

It will be apparent from the foregoing that, while particular forms of the invention have been illustrated and described, various modifications can be made without departing from the spirit and scope of the invention. For example, while the foregoing describes use of only one attachment system 24 within the graft 22, it is possible to use a plurality of attachment systems in accordance with the general principles of the present invention. Additionally, where appropriate, additional support structures 40, such as exemplified in FIGS. 4 through 7, may be used to maintain the patency of the graft's lumen, and to enhance the pressure between graft and vascular wall, without the simultaneous use of additional substantially rigid stents at the longitudinal position of such support structures.

Accordingly, it is not intended that the invention be limited, except as by the appended claims.

I claim:

1. A method for repairing an aortic vessel, comprising:
   implanting in the lumen of the vessel at a position superior of the renal arteries, a substantially rigid stent, the stent having a generally tubular configuration and configured to substantially resist expansion after deployment within the lumen of the vessel; and
   subsequent to the implanting step, deploying a prosthetic device within the vessel adjacent the stent, the prosthetic device comprising,
      an attachment system configured to engage the prosthetic device with the stent, the attachment system being positioned within the lumen of the stent,
      a graft located longitudinally separated from the attachment system, the graft being positioned inferior of the renal arteries, and
      ties connecting the attachment system to the graft, the longitudinal separation between the attachment system and the graft being a function of the length of the ties.

2. The method of claim 1, further comprising the step of configuring the stent to facilitate tissue ingrowth.

3. The method of claim 2, the attachment system of the prosthetic device further comprising hooks.

4. The method of claim 3, the stent further comprising a wall having a plurality of orifices, wherein the hooks of the attachment system are configured to protrude into the orifices of the stent.

5. The method of claim 1, the prosthetic device further comprising a support structure within the interior of the graft, wherein the support structure is configured to maintain patency of the graft to create a sealing engagement between the graft and the vessel.

6. A system for repairing a vessel, the vessel having a wall defining a lumen, the system comprising:
   a substantially rigid stent, the stent having a generally tubular configuration and configured to have a substantially fixed diameter after deployment within the lumen of the vessel; and
   a prosthetic device, the prosthetic device comprising,
      an attachment system, the attachment system being configured to engage the prosthetic device with the stent after the stent is placed in the lumen of the vessel, and a graft,
   wherein the attachment system is positioned so as to be longitudinally separated from the graft.

7. The system of claim 6, the attachment system of the prosthetic device further comprising hooks.

8. The system of claim 7, the stent further comprising a wall having a plurality of orifices, wherein the hooks of the attachment system are configured to protrude into the orifices of the stent.

9. The system of claim 8, wherein the hooks of the attachment system are further configured to penetrate the wall of the vessel.

10. The system of claim 6, wherein the attachment system of the prosthetic device is self-expanding.

11. The system of claim 10, wherein the stent is sufficiently rigid to substantially resist expansion induced by self-expansion forces from the attachment system.

12. The system of claim 10, wherein continued self-expansion of the attachment system after engagement of the prosthetic device with the stent is substantially precluded by the stent.

13. The system of claim 6, wherein the attachment system of the prosthetic device is balloon-expanded.

14. The system of claim 6, the prosthetic device further comprising ties to connect the attachment system to the graft, wherein the longitudinal separation between the attachment system and the graft is substantially a function of the length of the ties.

15. The system of claim 6, wherein the attachment system of the prosthetic device is formed from a frame which follows a generally undulating path.

16. The system of claim 15, the attachment system further comprising a plurality of superior apices and a plurality of inferior apices, the superior apices being connected to the inferior apices by connecting legs.

17. The system of claim 6, the stent further including a plurality of orifices.

18. The system of claim 17, wherein the orifices within the stent are adapted for tissue ingrowth and operate to provide the prosthetic device with mechanical support to resist downstream forces.

19. The system of claim 6, the prosthetic device further comprising a support structure configured within an interior of the prosthetic device.

20. The system of claim 19, wherein the support structure is adapted to maintain patency of the prosthetic device.

21. The system of claim 6, wherein the stent is adapted for tissue ingrowth and operates to provide the prosthetic device with mechanical support to resist downstream forces.

* * * * *